(12) United States Patent
Mackenzie et al.

(10) Patent No.: US 9,259,333 B2
(45) Date of Patent: Feb. 16, 2016

(54) MOUNTING PLATE ASSEMBLY FOR PROSTHETIC DEVICE

(71) Applicant: OSSUR hf, Reykjavik (IS)

(72) Inventors: Maitland Craig Mackenzie, Orlando, FL (US); Michael Patrick Tuttle, Titusville, FL (US)

(73) Assignee: OSSUR hf, Reykjavik (IS)

( * ) Notice: Subject to any disclaimer, the term of this patent is extended or adjusted under 35 U.S.C. 154(b) by 0 days.

(21) Appl. No.: 14/175,426

(22) Filed: Feb. 7, 2014

(65) Prior Publication Data

US 2014/0222165 A1    Aug. 7, 2014

Related U.S. Application Data

(60) Provisional application No. 61/761,951, filed on Feb. 7, 2013.

(51) Int. Cl.
*A61F 2/80* (2006.01)
*A61F 2/50* (2006.01)
*A61F 2/78* (2006.01)

(52) U.S. Cl.
CPC ............ *A61F 2/80* (2013.01); *A61F 2/5044* (2013.01); *A61F 2/7812* (2013.01); *A61F 2002/7875* (2013.01); *A61F 2002/805* (2013.01); *A61F 2002/807* (2013.01)

(58) Field of Classification Search
CPC ....... A61F 2/78; A61F 2/80; A61F 2002/802; A61F 2002/805; A61F 2002/807
See application file for complete search history.

(56) References Cited

U.S. PATENT DOCUMENTS

| 5,545,230 | A | | 8/1996 | Kinsinger et al. |
|---|---|---|---|---|
| 5,658,353 | A | * | 8/1997 | Layton ............................ 623/34 |
| 5,702,489 | A | | 12/1997 | Slemker |
| 6,063,125 | A | | 5/2000 | Arbogast et al. |
| 6,287,345 | B1 | | 9/2001 | Slemker et al. |

(Continued)

FOREIGN PATENT DOCUMENTS

| GB | 2 291 352 A | 1/1996 |
|---|---|---|
| WO | 2012/142627 A2 | 10/2012 |

OTHER PUBLICATIONS

International Search Report from International Application No. PCT/US2014/015329, mailed May 16, 2014.

*Primary Examiner* — Marcia Watkins
(74) *Attorney, Agent, or Firm* — Workman Nydegger

(57) ABSTRACT

A prosthetic device and a method for making the same includes a mounting plate assembly. The mounting plate assembly includes an inner housing having a first center channel defined along a central axis, an outer housing having a second center channel defined along the central axis, and a fluid regulator arranged between the inner and outer housings, and defined along the central axis. The prosthetic device includes a socket having a cavity and a distal portion whereat the mounting plate assembly is located.

The mounting plate assembly further including an inner mounting plate having a first center opening defined along the central axis, the first center opening arranged to receive at least a portion of the inner housing; and an outer mounting plate having a second center opening defined along the central axis, the second center opening arranged to receive at least a portion of the outer housing; wherein the inner and outer mounting plates define a plurality of corresponding holes for receiving a plurality of fasteners for securing to the inner and outer mounting plates.

15 Claims, 9 Drawing Sheets

(56) References Cited

U.S. PATENT DOCUMENTS

| | | |
|---|---|---|
| 6,361,569 B1 | 3/2002 | Slemker et al. |
| 6,689,171 B2 | 2/2004 | Slemker et al. |
| 6,979,355 B1 | 12/2005 | Slemker |
| 7,025,793 B2 | 4/2006 | Egilsson |
| 7,631,657 B2 | 12/2009 | Alley et al. |
| 7,771,487 B2 | 8/2010 | Mantelmacher |
| 7,947,085 B2 | 5/2011 | Haines et al. |
| 7,955,397 B2 | 6/2011 | Hoerner |
| 7,993,413 B2 | 8/2011 | Perkins et al. |
| 8,016,892 B2 | 9/2011 | Colvin et al. |
| 8,034,120 B2 | 10/2011 | Egilsson |
| 8,211,187 B2 | 7/2012 | Slemker et al. |
| 8,372,159 B2 | 2/2013 | Mackenzie |
| 2002/0116071 A1 | 8/2002 | Slemker et al. |
| 2007/0168045 A1* | 7/2007 | Slemker et al. ............. 623/34 |
| 2007/0213839 A1 | 9/2007 | Nachbar |
| 2008/0267698 A1* | 10/2008 | Rinkenberger et al. .... 403/322.2 |
| 2010/0094432 A1 | 4/2010 | Mackenzie |
| 2014/0058529 A1 | 2/2014 | Schober et al. |

* cited by examiner

MOUNTING PLATE ASSEMBLY FOR PROSTHETIC DEVICE

This application claims benefit of provisional application No. 61/761,951. The disclosure of the above named provisional application is incorporated herein by reference in its entirety.

FIELD OF THE DISCLOSURE

The present disclosure relates to the field of prosthetics, and more particularly to an attachment system for securing a prosthetic device to a patient.

BACKGROUND

Many types of prosthetic devices are available for amputees. These devices may be constructed for attachment to a mounting system arranged to secure the device to the wearer. Conventional mounting systems may include an open-ended socket for receiving and supporting an amputee's residual limb. In lower leg prostheses, straps and other fasteners are often provided for securing the prosthesis to the residual limb to accommodate walking mobility at least limitedly. The ability to achieve full use of a prosthetic limb is an important factor in both the physical and mental rehabilitation of an amputee.

Properly fitting and securing a prosthetic device to an amputee is often difficult because residual limbs can be various shapes and sizes and their volume may fluctuate. Older residual limbs may have experienced atrophy and are generally more conical in shape, while many newer residual limbs are slightly bulbous or cylindrical in shape. Residual limbs may be characterized by various individual characteristics, including the volume and shape of the limb, scars, skin grafts, bony prominences, edema or soft tissue configurations. Conventional prosthetic device mounting systems do not fit snugly on an amputee and are typically not comfortable to wear.

A proper fit of the prosthetic device on a residual limb is essential to ensure adequate mobility and safety. In walking, compressive loading of the soft residual limb tissue can cause blisters, sores, chafing, and other undesirable skin irritation problems. Conventional mounting systems that attempt to correct these deficiencies by including additional soft padding within the socket are disadvantageous since the extra material can interfere with forming an optimal connection.

One way in which a prosthetic device can be attached to a residual limb is by using suction or vacuum pressure. Such an arrangement often includes using liners worn on the residual limb. These liners can be made from a soft, stretchy material that acts as an interface with the prosthesis. Once the liner is on, the residual limb can then slide into a hard socket made to fit the shape of the residual limb.

When attaching a prosthetic device to a wearer, the socket must be securely fitted to the limb to hold it in place during movement. Maintaining stability for the wearer is a common problem, since many existing anchoring systems use a single attachment point to hold the residual limb in place. This type of arrangement may lead to extraneous pivoting, rotating, and shifting of the residual limb, especially during ambulation for lower body limbs, such as lower leg and knee prosthetics.

It is important to be able to periodically adjust the anchoring system since the mass of the limb may change throughout the day. Residual limbs can change size due to swelling or contracting depending on factors such as how they are used, their frequency of use, and the temperature. Minor protuberances inside the socket can be uncomfortable and cause unbearable pain to an amputee.

Some conventional anchoring systems with generally cylindrical sockets may be secured to a residual limb via a radial pressure fit. This type of system is not ideal since radial pressure imposed on a limb received in a hard socket squeezes it unevenly and adds to the discomfort felt by the amputee. The fit obtained may not be secure since radial pressure can cause the limb to pop out of the socket over a day making the system unreliable for a wearer.

Alternatively, Velcro or Chicago screws have traditionally been used to attach an insert to a socket retainer. This arrangement is functional when using a standard expulsion or vacuum system sealed proximally with a sealing sleeve. Modern sockets with flexible liners may have cutouts over boney prominences or utilize internal socket seals. These newer sockets cannot accommodate a flexible insert in combination with a vacuum or expulsion valve because the vacuum or expulsion system is housed in the outer retainer. This is undesirable because air would enter the system proximally between the inner flexible insert and the rigid retainer. For a vacuum or expulsion system to work, the vacuum or expulsion system in the distal portion of the retainer would have to be connected to the flexible inner insert distally as in the present disclosure.

When a lower limb amputee ambulates using a conventional prosthesis, air inside the socket may cause the prosthesis to slip from the amputee during the swing phase of a normal gait cycle. This causes an accelerated impact of the residual limb at the bottom of the socket when the heel hits the floor. By removing air from the cavity, the prosthesis can be held closer to the residual limb during the swing phase, thus reducing the accelerated impact at heel strike. There are many ways to remove the air, including an expulsion valve. Conventional expulsion valves, however, are installed in or through the walls of the socket, which is not optimal.

There are many types of one-way valves, including spring valves. Spring valves use a spring to urge a stopper to resist air from traveling in one direction while allowing the air to travel in the other direction. The disadvantage of using spring valves is that air must accumulate enough force to overpower the spring and open the valve. The consequence of this is that the spring will close the valve before most air escapes the socket, which is called "cracking pressure." It is not desirable to allow air to come back through the valve as weight is relieved from the prosthesis during the swing phase of ambulation. This cycle is repeated as the amputee walks, thus creating a vacuum. Another downside with a vacuum suspension system is that any significant loss of vacuum may cause separation of the prosthetic socket from the residual limb.

It is advantageous to provide a mounting plate assembly providing superior comfort and stability to an amputee. It is beneficial to provide a mounting plate assembly offering improved reliability by limiting extraneous up and down motion, pivoting, rotation and shifting during use. Further, it is advantageous to provide extra durability to the prosthesis. The present disclosure addresses all of these aforementioned needs.

SUMMARY

According to embodiments described, a mounting plate assembly is provided for securing a prosthetic device to a residual limb of an amputee. The mounting plate assembly preferably includes a pair of mounting plates for attaching to a multi-layered socket defining an opening. The embodiments make it comfortable for an amputee to wear a prosthetic device while improving an amputee's mobility during use.

Preferably, the mounting plate assembly can be used with a lower leg and/or knee prosthesis to provide an amputee a way to walk without additional assistance. The socket allows fluid to be evacuated from its interior via a fluid regulator located between the pair of mounting plates. By maintaining fluid communication between the cavity and the mounting plate assembly, the fluid regulator may assist in securing a residual limb within the cavity via expulsion suspension. The weight exerted by an amputee on the prosthesis while walking urges air out of the socket through a one-way valve. This creates an air-tight and secure fit between the cavity and a residual limb, and is maintained as weight is relieved from the prosthesis during the swing phase of ambulation.

Vacuum assistance can secure a residual limb to the mounting plate assembly by using a vacuum source to draw air out from the cavity. The air is expelled through the fluid regulator and then evacuated from the mounting plate assembly. The fluid regulator can serve as a safety measure between the cavity and a vacuum source since the expulsion suspension would continue to secure the residual limb within the socket even if the vacuum source fails.

The embodiments are arranged to minimize extraneous up and down motion, pivoting, rotation, and shift during ambulation, of which suspension systems are often susceptible. According to the embodiments, the weight of the amputee during ambulation will create enough force to push or expel air from the interior socket space through the one-way valve. This will help keep the residual limb secured to the socket via an associated vacuum pressure.

The embodiments provide a thermoplastic solution to a fully laminated socket-type system. The cavity of the present disclosure includes both an elastic inner portion and stiff outer portion attached to the mounting plate assembly. The outer portion provides additional support to maintain the socket's fit on a residual limb by providing a seal between the inner portion and an inner mounting plate.

If air enters the cavity due to a leak in the inner socket portion, the strength of the socket's fit to a residual limb would be diminished if not for the sealing approach of the embodiments. The elastic inner portion of the socket with the stiff outer portion is arranged so the inner portion can be held in place distally while still maintaining a fluid-tight seal with the stiff outer portion. This further allows for the vacuum/expulsion system to act on the cavity rather than the space between the inner and outer socket portions.

In a preferred embodiment, the mounting plate assembly for a prosthetic device includes an inner housing having a first center channel defined along a central axis, an outer housing having a second center channel defined along the central axis, and a fluid regulator connected to the inner and outer housings, and generally defined along the central axis.

An inner mounting plate has a first center opening defined along a central axis and is arranged to receive at least a portion of the inner housing. The inner housing may define a first engagement portion arranged to be received by and closely conform to at least a portion of the first center opening. The inner housing may define a square or circular shape, with the first center opening formed centrally within the given shape.

An outer mounting plate includes a second center opening defined along a central axis. The second center opening may be arranged to receive at least a portion of the outer housing. The inner and lower mounting plates may be spaced apart by a clearance which may be filled in with material from the prosthetic socket, such as the outer retainer. The inner and outer mounting plates define a plurality of corresponding holes for receiving a plurality of fasteners for securing to the inner and outer mounting plates.

The outer housing preferably defines a second engagement portion arranged to be received and closely conform to at least a portion of the second center opening. The second center opening defines a recessed portion into which the second engagement portion fits. A bottom surface of the outer housing may be arranged flush relative to a bottom surface of the outer mounting plate. A first lower seal may be carried by the second engagement portion and secured against a portion of the outer mounting plate.

The outer housing may include a shoulder portion defining a base of the outer housing, a second engagement portion extending upwardly from the shoulder portion, and a plurality of cylindrical portions extend from the second engagement portion. At least two of the cylindrical portions have a different diameter from one another with a lower cylindrical portion having a greater diameter than at least one upper cylindrical portion. The plurality of cylindrical portions are arranged to extend within and be received by the first center channel.

The second center channel preferably extends through the entire outer housing. A second lower seal is carried by the at least one upper cylindrical portion, and is arranged to engage the first center channel. The at least one upper cylindrical portion defines first and second segments spaced apart by a peripheral groove adapted to receive the second lower seal.

A method of manufacturing an attachment system for a prosthetic device may comprise creating an inner flexible insert by heating a thermoplastic, blister-forming the thermoplastic over a shape, forming a space in the inner flexible insert adapted to hold an inner housing, and forming a rigid outer retainer over the inner housing. The method may include axially securing a fluid regulator between the inner housing and an outer housing.

BRIEF DESCRIPTION OF THE DRAWINGS

These and other features, aspects, and advantages of the present disclosure will become better understood regarding the following description, appended claims, and accompanying drawings.

Figure 1:
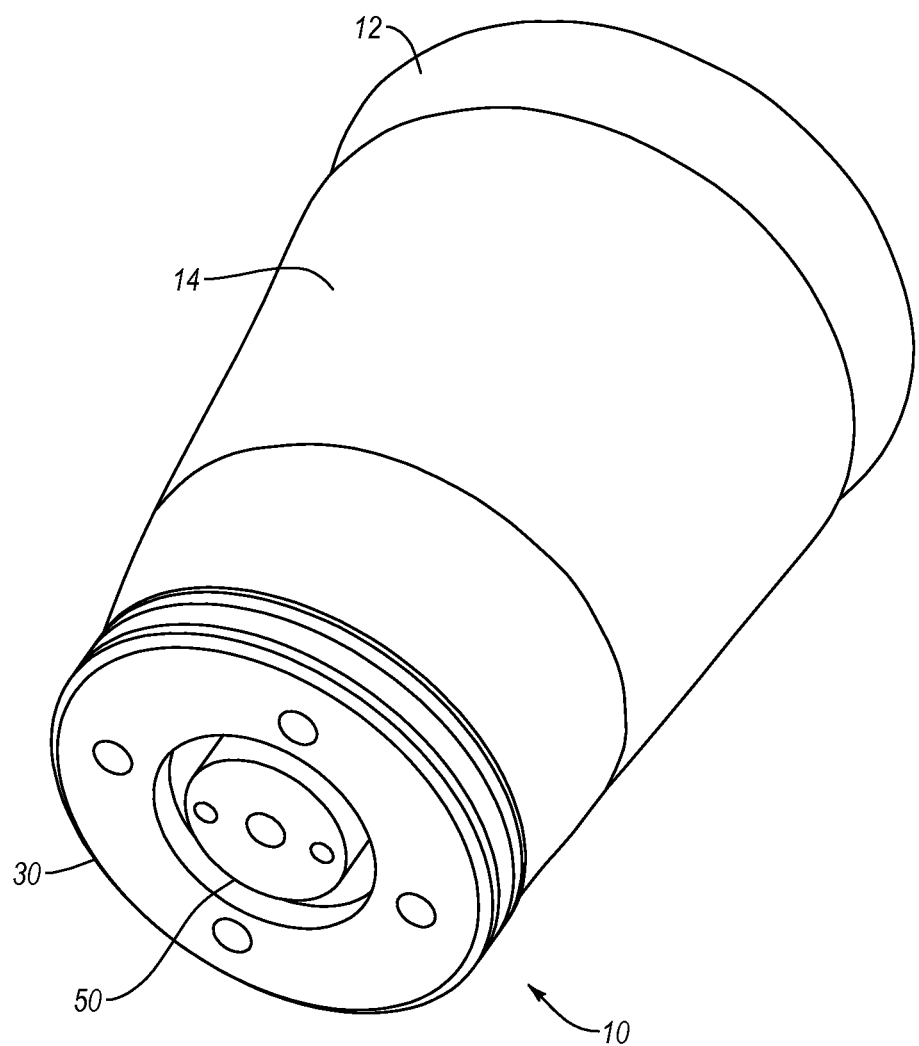
FIG. 1 is a perspective view of a mounting plate assembly securely connected to a socket according to an embodiment of the disclosure.

The figures are not necessarily drawn to scale, but instead are drawn to provide a better understanding of the components and are not intended to be limiting in scope, but rather to provide exemplary illustrations. The figures illustrate exemplary embodiments of a mounting plate assembly for a prosthetic device and the components, and in no way limit the structure or configuration of a mounting plate assembly for a prosthetic device according to the present disclosure.

DETAILED DESCRIPTION OF VARIOUS EMBODIMENTS

A. Overview

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

Unless a term is expressly defined in this disclosure to possess a described meaning, there is no intent to limit the meaning of such term, either expressly or indirectly, beyond its plain or ordinary meaning.

The attachment system is configured for use with a prosthetic device, such as a lower leg and/or knee prosthesis. It should be remembered that the same concepts and methods described may be similarly employed for mounting plate assemblies used on other prosthetic devices and are not limited solely to the anatomical locations discussed.

B. Definitions

For ease of understanding the embodiments of an attachment system for a prosthetic device as disclosed, a description of a few terms, when used, is necessary.

As used, the terms "proximal" and "inner" have their ordinary meaning and refer to a location situated next to or near the point of attachment or origin or a central point or located toward the center of the body. Likewise, the terms "distal" and "outer" have their ordinary meaning and refer to a location situated away from the point of attachment or origin or a central point or located away from the center of the body.

The terms "rigid" and "flexible" may be used to distinguish characteristics of portions of certain features of the prosthetic device. The term "rigid" should denote that an element of the device is generally devoid of flexibility. Within the context of sockets that are "rigid," it is intended to indicate that they do not lose their overall shape when force is applied. The term "flexible" should denote that features can bend into retained shapes, or the features do not retain a general shape but continuously deform when force is applied.

C. Embodiments of the Attachment System

The following description refers to an attachment system for allowing a wearer of a prosthetic device to function with full or near full mobility. A mounting plate assembly for securing a prosthesis to a residual limb, such as a knee, of an amputee is described. Features of this disclosure, however, may apply to a mounting plate assembly for use with any limb or joint area that may benefit from expulsion suspension or vacuum assistance. Features of the present disclosure are directed to a mounting plate assembly and associated methods of making and using a mounting plate assembly. It should be appreciated that embodiments of the disclosure may be incorporated for use with different prosthetic appliances, such as transtibial, transfemoral, transradial, and transhumeral prostheses.

Figure 2:
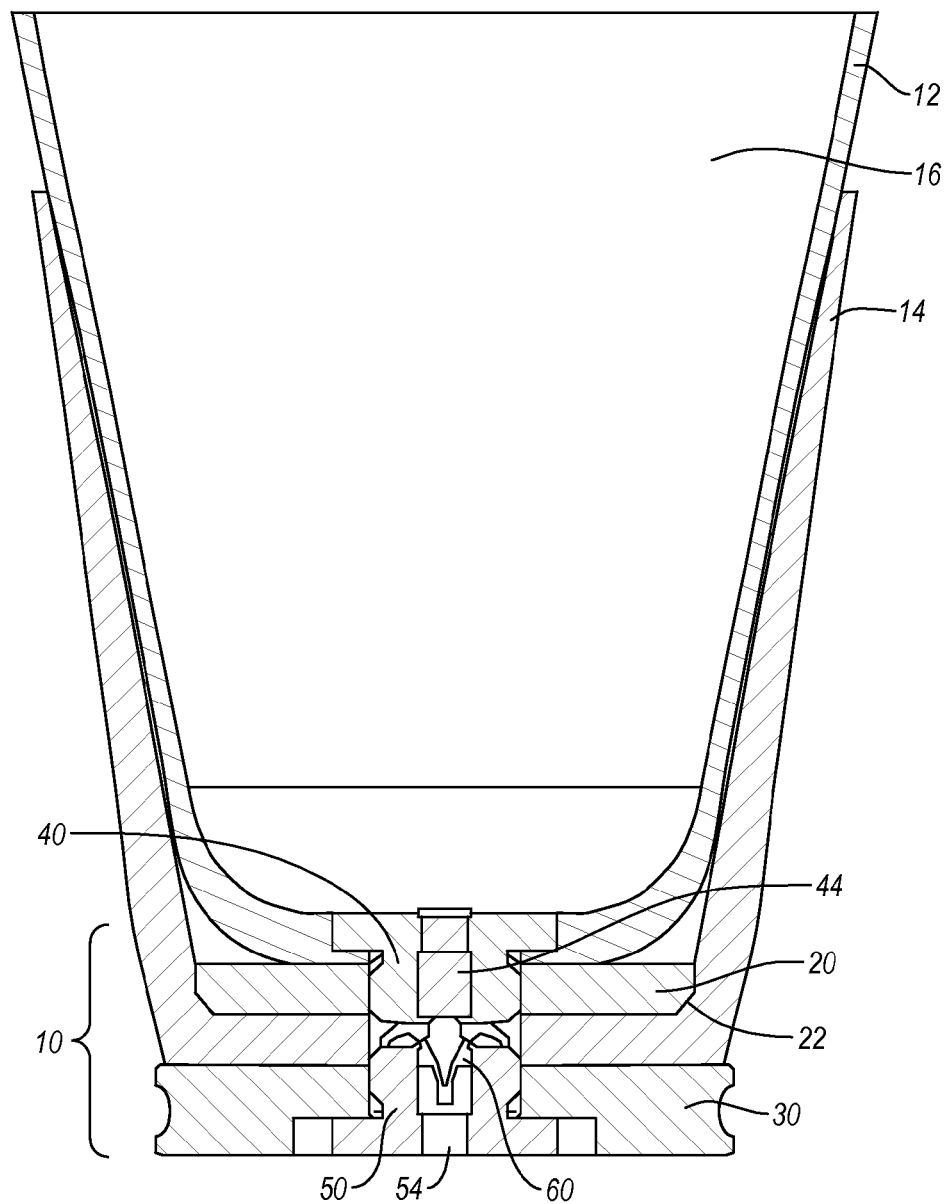
FIG. 2 is a front cross-sectional view of the mounting plate assembly according to the embodiment of FIG. 1.

In reference to FIGS. 1 and 2, a mounting plate assembly 10 is shown for use with a prosthetic socket for receiving a residual limb, as appreciated by those skilled in the art. The socket comprises an inner flexible insert 12 having an open proximal end defining a cavity 16 for receiving a residual limb of an amputee. A liner may preferably cover the residual limb when inserted into the cavity 16.

The socket further comprises a rigid outer retainer 14 having an open proximal end for receiving both the inner flexible insert 12 and the residual limb. Both the inner flexible insert 12 and the rigid outer retainer 14 have at least one opening at a distal end for attachment to the mounting plate assembly 10. The mounting plate assembly 10 includes an inner mounting plate 20 and an inner housing 40, between which the inner flexible insert 12 is secured.

Figure 3:
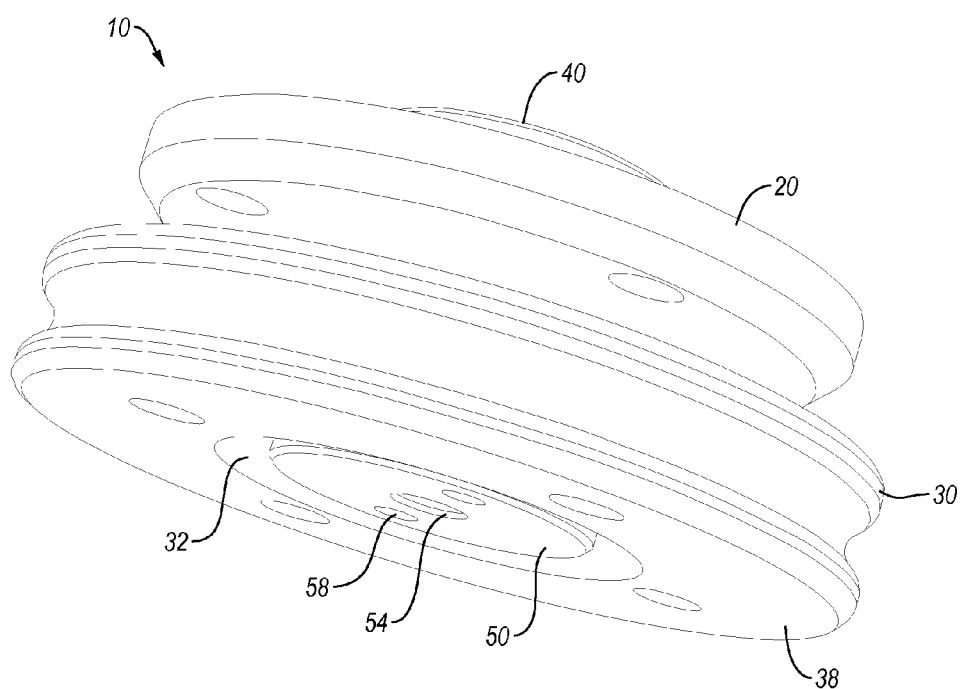
FIG. 3 is a perspective view of the mounting plate assembly according to the embodiment of FIG. 1 without the socket attached thereto.
Figure 4:
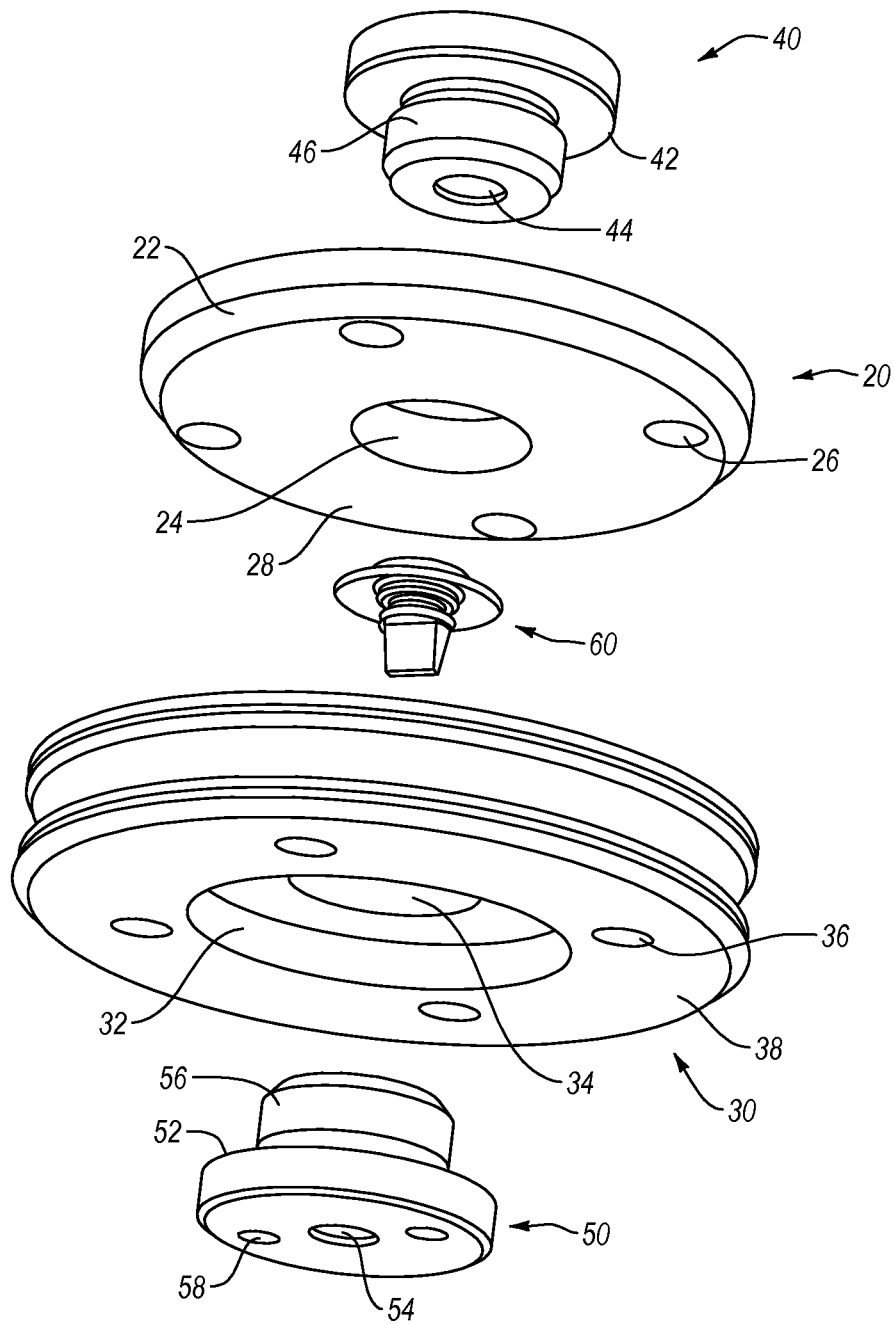
FIG. 4 is an exploded perspective view of the mounting plate assembly in FIG. 3.

Turning briefly to FIGS. 3 and 4, the inner mounting plate 20 is generally circular in shape and has a recessed portion 22, such as a chamfer or fillet, located along an outer periphery of its bottom surface 28. The inner mounting plate 20 includes a central threaded opening 24 for releasable attachment to the inner housing 40. The inner housing 40 is provided with a shoulder portion 42 at its proximal end and a first engagement portion 46 oppositely at its distal end. The first engagement portion 46 may be correspondingly threaded for securing to the central opening 24 of the inner mounting plate 20. Both the shoulder portion 42 and the first engagement portion 46 are generally cylindrical, and the diameter of the shoulder portion 42 is greater than that of the first engagement portion 46.

When assembled, as illustrated in FIG. 2, the first engagement portion 46 of the inner housing extends through an opening at the distal end of the inner flexible insert 12 toward the top surface of the inner mounting plate 20 and threadedly engages the central threaded opening 24 of the inner mounting plate 20. This connection laterally secures the inner flexible insert 12 to the mounting plate assembly 10. The shoulder portion 42 of the inner housing 40 anchors the distal end of the inner flexible insert 12 directly to the top surface of the inner mounting plate 20, axially securing the inner flexible insert 12 to the mounting plate assembly 10.

To prevent irritation to the residual limb, the first engagement portion 46 is preferably sufficiently tightened to the inner mounting plate 20 so that the top surface of the inner housing 40 at its proximal end lies flush with the interior surface of the inner flexible insert 12. This ensures that the inner housing 40 will not protrude into the cavity 16 if causes discomfort to a wearer.

A generally cylindrical center channel 44 axially extends through the entire length of the inner housing 40, including through both the shoulder portion 42 and the first engagement portion 46. Upon securing the inner housing 40 to the inner mounting plate 20 the center channel 44 becomes axially aligned with the mounting plate assembly 10 to maintain a fluid passageway from the cavity 16 through the inner mounting plate 20.

The mounting plate assembly 10 includes an outer mounting plate 30, which is generally circular in shape and has a central threaded opening 34 for attachment to an outer housing 50. The outer housing 50 is provided with a shoulder portion 52 at its proximal end and a second engagement portion 56 at its opposite distal end. Both the shoulder portion 52 and the second engagement portion 56 are generally cylindrical, and the diameter of the shoulder portion is preferably greater than that of the second engagement portion 56.

The second engagement portion 56 may be correspondingly threaded for releasably securing to the central opening 34 of the outer mounting plate. When assembled, the second engagement portion 56 threadedly secures into the bottom surface 38 of the outer mounting plate 30 through the central threaded opening 34. The bottom surface 38 of the outer mounting plate 30 forms a central recessed portion 32 defining a cylindrical cavity surrounding the central threaded opening 34, and which is adapted to fit the shoulder portion 52 of the outer housing 50.

As illustrated in FIG. 2, when the outer housing 50 is inserted into central opening 34 of the outer mounting plate 30, an inner edge of the shoulder portion 52 of the outer housing 50 may contact an inner edge at the bottom the cavity 32 to prevent further ingress of the outer housing 50 into the outer mounting plate 30. In a preferred embodiment, the thickness of the shoulder portion 52 is configured to match the depth of the cavity 32 such that the outer surface of the outer housing 50 at its proximal end becomes flush with the bottom surface 38 of the outer mounting plate 30 when the outer mounting plate 30 and the outer housing 50 are secured together. It should be appreciated, however, that other configurations are acceptable, such as having a shoulder portion of the outer housing thicker than the depth of the cavity so the proximal end of the outer housing protrudes outwardly from the bottom surface of the outer mounting plate when secured thereto.

The central recess 32 is directly adjacent to and axially aligned with the central opening 34 of the outer mounting plate 30. A generally cylindrical center channel 54 axially extends through the entire length of the outer housing 50, including through both the shoulder portion 52 and the threaded portion 56. Upon securing the outer housing 50 to the outer mounting plate 30 the center channel 54 preferably becomes axially aligned with the mounting plate assembly 10 to maintain a fluid passageway through the outer mounting plate 30.

The distal end of the rigid outer retainer 14 is secured between the top surface of the outer mounting plate 30 and the bottom surface 28 of the inner mounting plate 20 when the mounting plate assembly 10 is fully assembled. The opening at the distal end of the rigid outer retainer 14 is axially aligned with both the central threaded opening 24 of the inner mounting plate 20 and the central opening 34 of the outer mounting plate 30.

In a preferred embodiment, the recessed portion 22 of the inner mounting plate 20 replaces what would otherwise be a sharp edge along a periphery of the bottom surface 28. This recessed portion 22 helps reduce damage to the rigid outer retainer 14 by accommodating its shape and allowing the rigid outer retainer to extend in the same direction adjacent to the inner flexible insert 12.

The inner mounting plate 20 may include a pattern, such as a four-bolt pattern, of threaded securing openings 26 for attachment to a matching pattern of non-threaded alignment holes 36 on the outer mounting plate 30. The securing openings 26 are the same size as the alignment holes 36 so a fastener, such as a bolt or screw, will fit into each corresponding opening to connect the inner and outer mounting plates together. When assembling the mounting plate assembly 10, a fastener is first inserted into one of the alignment holes 36 from the bottom surface 38 of the outer mounting plate 30 such that an end of the fastener extends through and protrudes from a top surface of the outer mounting plate 10 opposed from the bottom surface 38. The protruding portion of the fastener can then engage a corresponding securing opening 26 of the inner mounting plate 20 from its bottom surface 28.

Figure 5:
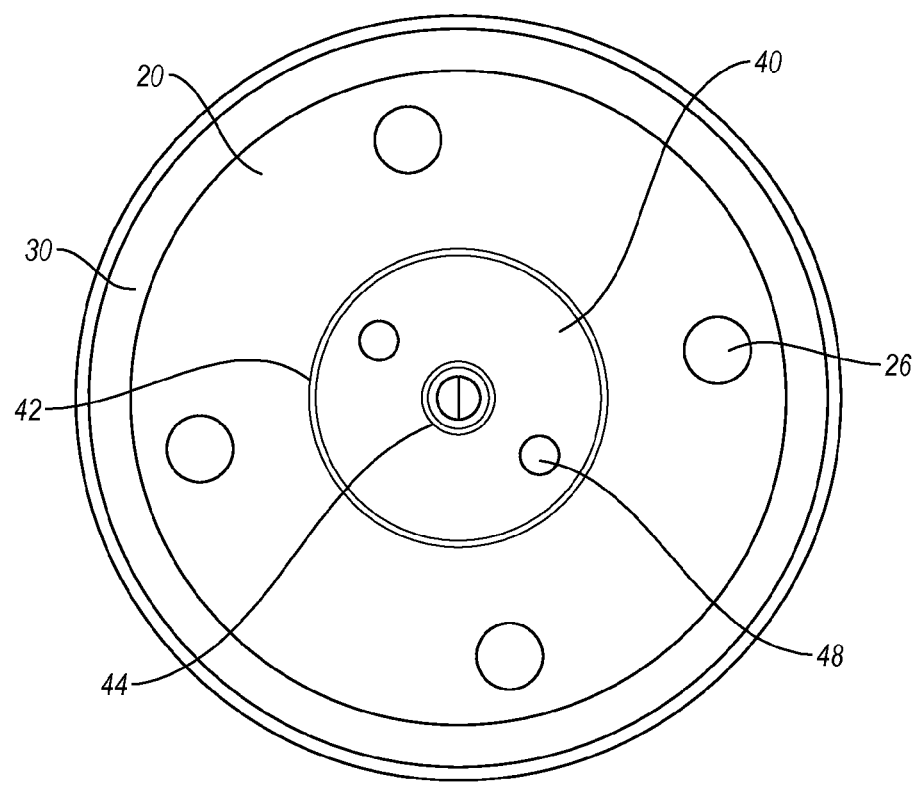
FIG. 5 is a top plan view of the mounting plate assembly in FIG. 3.
Figure 6:
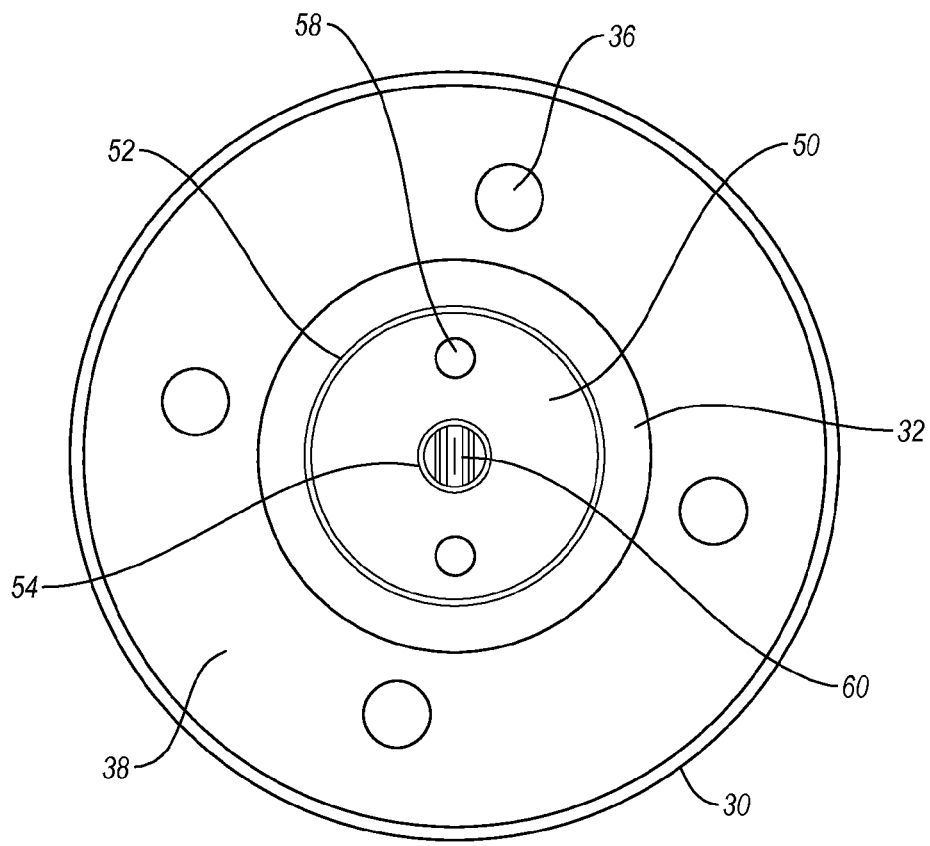
FIG. 6 is a bottom plan view of the mounting plate assembly in FIG. 3.

Turning to FIG. 5, various recesses 48 may be in the shoulder portion 42 of the inner housing 40 for receiving a corresponding projection of a tool to assist in tightening the inner housing 40 into the central threaded opening 24 of the inner mounting plate 20. FIG. 6 shows similar recesses 58 may be in the shoulder portion 52 of the outer housing 50 for receiving a corresponding projection of a tool to assist in tightening the outer housing 50 into the central threaded opening 34 of the outer mounting plate 30.

Figure 7:
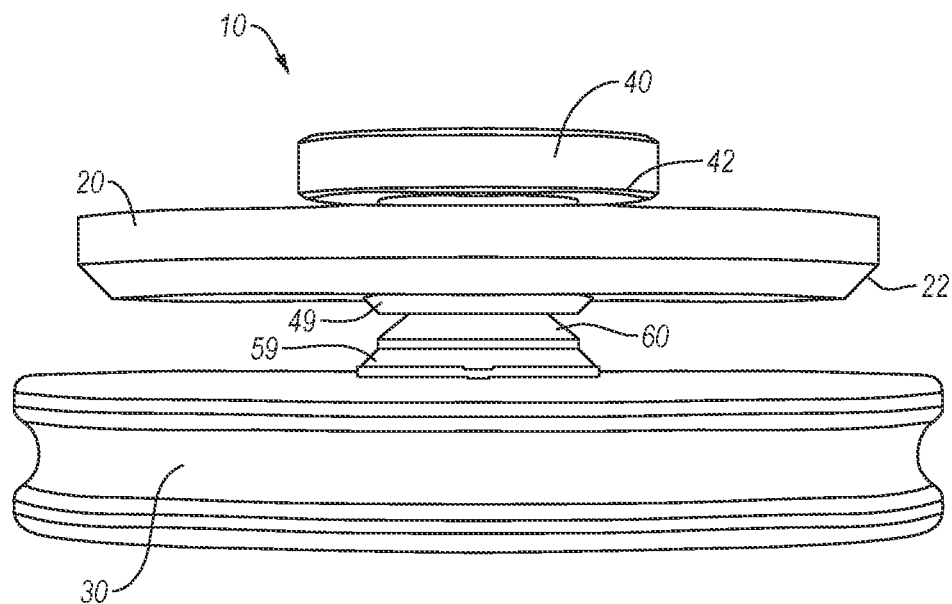
FIG. 7 is a side elevational view of the mounting plate assembly in FIG. 3.
Figure 8:
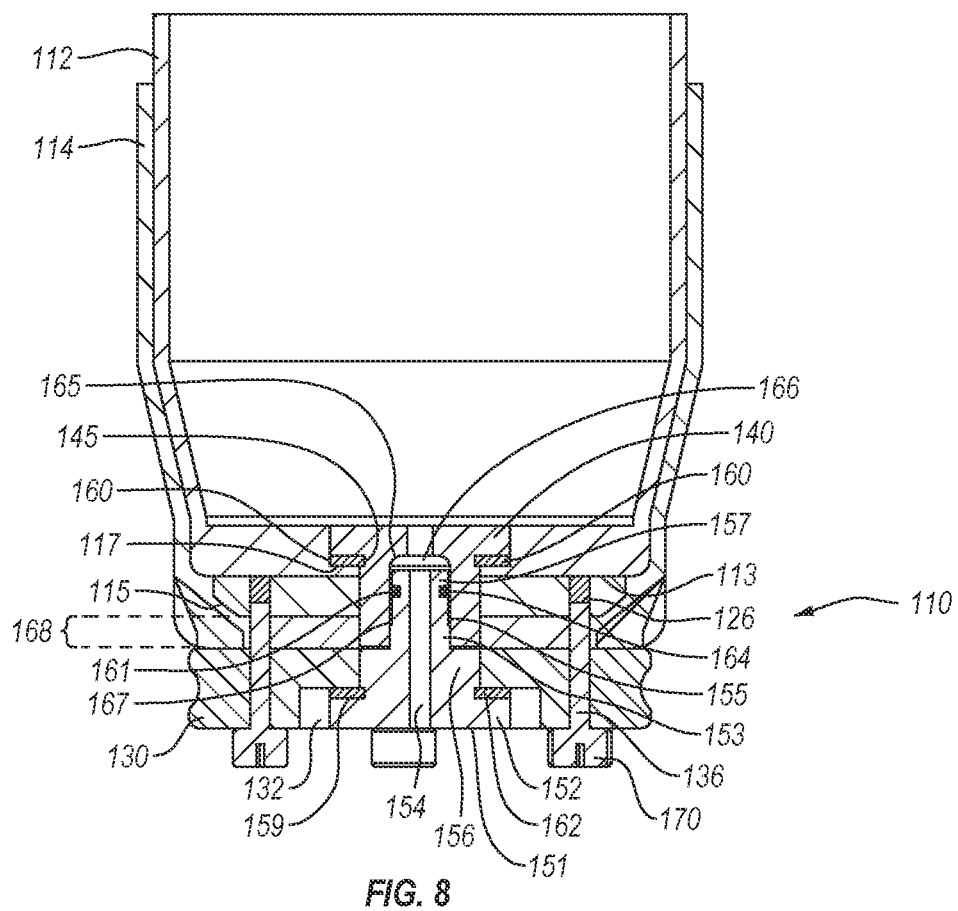
FIG. 8 is a front cross-sectional view of another embodiment of the mounting plate assembly.
Figure 9:
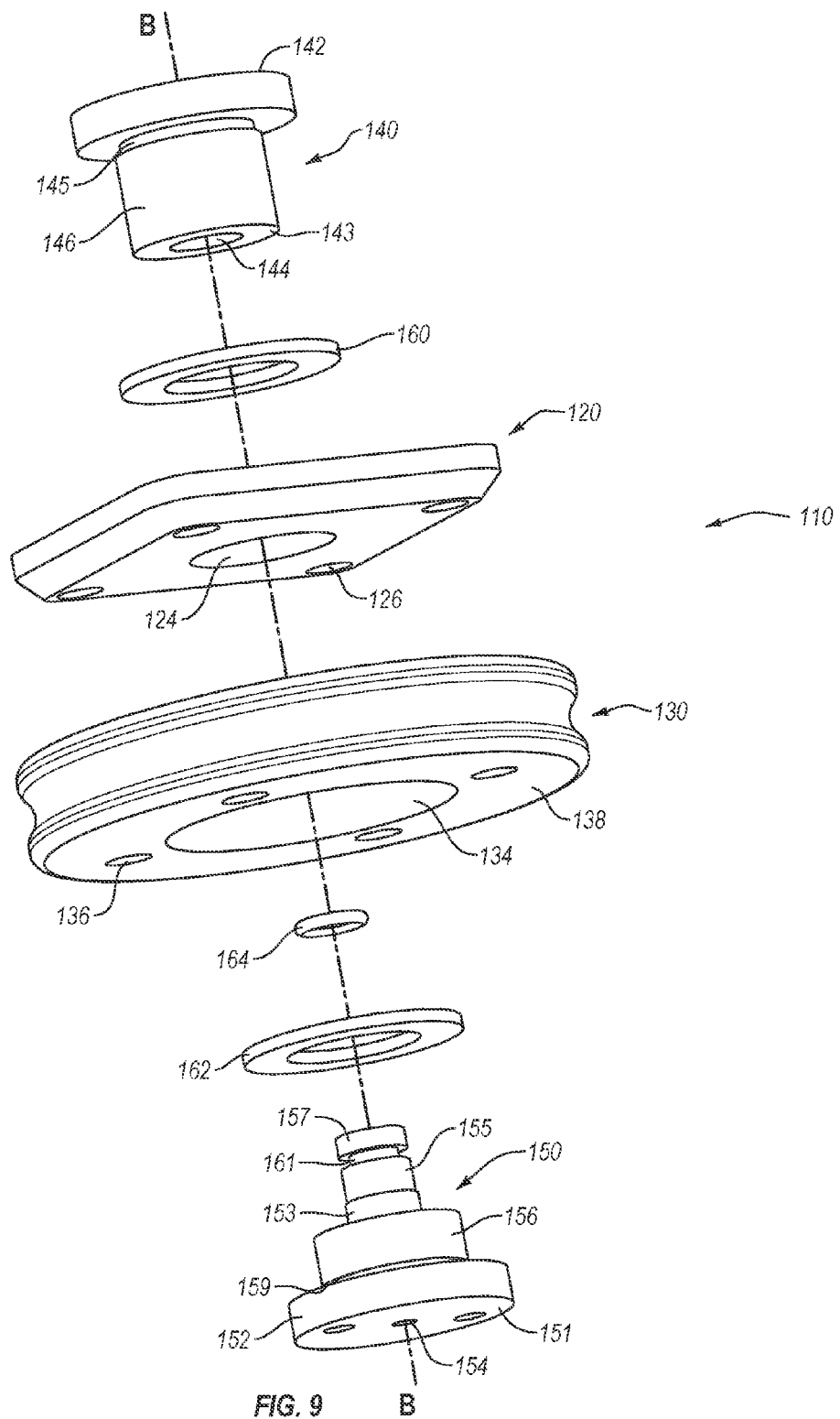
FIG. 9 is an exploded perspective view of the mounting plate assembly in FIG. 8.

When the mounting plate assembly 10 is assembled, it will be appreciated that the central threaded opening 24 of the inner mounting plate is axially aligned with the central opening 34 of the outer mounting plate 30 along axis A-A. The center channel 44 of the inner housing 40 is likewise axially aligned with center channel 54 of the outer housing 50. This alignment permits fluid communication between the cavity 16 and the center channels 44, 54 of the inner and outer housing, respectively. To regulate the flow of fluid, a fluid regulator 60 may be located between the inner and outer mounting plates 20, 30, as illustrated in FIGS. 2 and 7.

The fluid regulator 60 preferably prohibits air, moisture, and any other contaminate from entering the cavity 16 from outside of the mounting plates. Instead it ensures that the only air that can enter the mounting plate assembly 10 is from the cavity 16. The fluid regulator 60 is secured within the mounting plate assembly 10 via compression between a first and second compression end 49, 59 of the inner and outer housings 40, 50, respectively.

A separate o-ring or rubber compression washer can be provided for sealing engagement between the fluid regulator 60 and each respective compression end 49, 59 of the inner and outer housing. This configuration prevents fluid from leaking between the inner and outer mounting plates 20, 30. Even if a potential leak occurs, any air that might escape into the space between the inner flexible insert 12 and the rigid outer retainer 14 would not compromise the amputee's suspension since the air could not enter the cavity 16 due to the tight seal created by the resulting compression. This arrangement may cause more air being expelled from the cavity 16, thus decreasing the space between the distal end of the amputee's residual limb and the bottom of the socket. This could produce the added benefit of making the socket more comfortable for the amputee to wear by reducing the accelerated impact at heel strike during ambulation.

The fluid regulator 60 may preferably be a one-way expulsion valve, such as a rubber duckbill valve. This allows for quick air expulsion and easy cleaning. Alternatively, the fluid regulator may be an internal socket seal, such as in U.S. Pat. No. 7,025,793, granted on Apr. 11, 2006, U.S. Pat. No. 8,034,120, granted Oct. 11, 2011, and U.S. Pat. No. 8,372,159, granted on Feb. 12, 2013, each incorporated herein by their entirety.

A rubber duckbill valve preferably has a low cracking pressure of about 0.2 psi to accommodate the securing compressive forces supplied by the inner and outer housings. The first and second compression ends 49, 59 of the inner and outer housings act to compress an engagement flange on the duckbill valve to further help reduce or eliminate any leak that could occur between the valve and each adjacent housing. Conventional valve arrangements located in the distal portion of a socket do not adequately seal for this type of leak.

The discharge end of the duckbill valve may extend into the center channel 54 of the outer housing 50, as illustrated in FIG. 2. When the inner housing 40 is engaged with the central threaded opening 24 of the inner mounting plate 20, the center channel 44 provides fluid communication between the cavity 16 and the fluid entrance portion of the duckbill valve 60. Fluid communication is provided between the expulsion end of the duckbill valve 60 and the center channel 54 of the outer housing 50 when the outer housing is engaged with the central threaded opening 34 of the outer mounting plate 30.

A benefit of maintaining fluid communication through the entire mounting plate assembly 10 is that the fluid regulator 60 located inside can provide assistance for securing a residual limb within the cavity 16, such as by expulsion suspension. The weight exerted by an amputee on the prosthesis while walking pushes air in the cavity 16 through the one-way valve. An air-tight securing fit between the cavity and a residual limb is maintained as weight is relieved from the prosthesis during the swing phase of walking. If air enters the cavity during the swing phase, it is subsequently expelled once the amputee reapplies weight on the prosthesis.

Alternatively, vacuum assistance can secure a residual limb to the mounting plate assembly 10. Such vacuum assistance can be performed by using a vacuum source attached to the mounting plate assembly 10. An expulsion plate, a seal plate, or a vacuum spacer may optionally be provided for removable attachment to the outer mounting plate 30 to connect the vacuum source. When the vacuum source is used, air is drawn from the cavity 16 through the fluid regulator and center channels 44, 54 of the inner and outer housing 40, 50, and then evacuated from the mounting plate assembly 10.

The vacuum source may evacuate air in several ways, including via a hand pump, an electronic pump, or a mechanical pump activated by the amputee's walking motion. The fluid regulator 60 preferably may serve as a safety measure between the cavity 16 and any vacuum source. If the vacuum source fails, expulsion suspension would continue to secure a residual limb to the cavity 16. The fluid regulator is placed between the inner and outer housings 40, 50 to prevent air from entering into the cavity that may compromise the amputee's suspension if a leak in the seal plate occurs or vacuum spacer.

Manufacturing the mounting plate assembly 10 as described for use with a prosthetic socket advantageously offers a thermoplastic solution to a lamination system. The inner flexible insert 12 and the rigid outer retainer 14 are attached to the mounting plate assembly 10 during the manufacturing process. The inner flexible insert 12 may be made by first heating a thermoplastic and then blister-forming it over a plaster positive cast in the shape of a patient's residual limb. A dummy insert is placed on the distal end of the cast to form a space in the distal portion of the flexible insert 12 adapted to accommodate an inner housing 40. The inner housing 40 then replaces the dummy insert, and its first engagement portion 46 is connected to the central threaded opening 24 of the inner mounting plate 20.

A dummy screw is provided in each securing opening 26 of the inner mounting plate 20. A rigid plastic or laminate is then formed over the inner housing 40 and inner mounting plate 20 to create the rigid outer retainer 14. The presence of the inner housing 40 helps form a space in the distal portion of the rigid outer retainer 14 to preserve fluid communication therethrough, and the dummy screws serve as thickness spacers. This is accomplished by heating a thermoplastic material, such as polyethylene or polypropylene, until it is formable, and then stretching it over the inner mounting plate 20 to accommodate the shape of a residual limb.

The recessed portion 22 of the inner mounting plate 20 prevents the thermoplastic material from being cut by a sharp edge when stretched. The rigid plastic or laminate is accordingly ground down to reveal the dummy screws so an outer mounting plate 30 can be bolted directly to the inner mounting plate 20 such that each bolt is inserted through an alignment hole 36 from the bottom surface 38 of the outer mounting plate 50 and into a corresponding securing opening 26 on the inner mounting plate 20. The fluid regulator 60 and rubber compression washers can be axially secured inside the central fluid passageway between each mounting plate via compression between the inner housing 40 and an outer housing 50.

Referring to another embodiment of the mounting plate assembly 110, the system includes an insert 112 and an outer retainer 114 similar to the components in the embodiment of FIG. 1 for forming a socket. The mounting plate assembly 110 likewise includes an inner mounting plate 120, an outer mounting plate 130, an inner housing 140 and an outer expulsion housing 150. A fluid regulator (not shown) may be disposed between the inner and outer housings 140, 150 in a manner similar to the embodiment of FIG. 1.

The inner mounting plate 120 may be arranged in a square configuration for more ably securing between the inner and outer retainers 112, 114. In this embodiment, the outer retainer defines a recess 115 adapted to receive the inner mounting plate 120. The inner retainer 112 has a lower surface 113 arranged flush against an upper surface of the inner mounting plate 120, such that the inner mounting plate 120 is generally received in its entirety within the recess 115.

In this embodiment, a plurality of seals, such as o-ring gaskets, is used to account for fluctuations in both the fabrication process, such as varying thicknesses of plastic during hand modification of the insert and the outer retainer, and during wear. The inner and outer housings are configured and dimensioned accordingly to compensate for non-uniform thicknesses.

The inner housing 140 is arranged with a peripheral groove 145 located below the shoulder portion 142 and above the first engagement portion 146. The peripheral groove 145 is adapted to receive and retain a first upper seal 160 arranged to abut a recessed surface 117 of the insert 112. The inner housing 140 defines a center channel 144 dimensioned longer than the center channel 44 in the embodiment of FIG. 1, which requires the first engagement portion 146 be lengthened over the first engagement portion 46 of the embodiment of FIG. 1.

The inner mounting plate 120 generally having a square profile defines an opening 124 into which the first engagement portion 146 extends. The outer mounting plate 130 defines an opening 134 and a bottom surface 138. The outer mounting plate 130 preferably includes a recessed portion 132 as defined by the embodiment of FIG. 4. As with the embodiment of FIG. 1, a clearance may be defined between the inner and outer mounting plates 120, 130 and formed from material of the outer retainer 114.

The outer housing 150 defines a shoulder portion 152, a second engagement portion 156. A third peripheral groove 159 is defined between the shoulder portion 152 and the second engagement portion 156 and is adapted to snugly receive a first lower seal element 162. The first lower seal 162 is configured to engage the surfaces of the recessed portion 138 of the outer mounting plate 130, and a bottom surface 151 of the outer housing 150 is generally flush with the bottom surface 138 of the outer mounting plate 130.

The outer housing 150 further defines an upper portion formed from a plurality of cylindrical segments 153, 155, 157. The first cylindrical segment 153 extends from the second engagement portion 156 and has a diameter closely matching a diameter of the central channel 144. A second cylindrical segment 155 extends from an upper end of the first cylindrical segment 153, and has a diameter slightly less from the first cylindrical segment 153. A third cylindrical segment 157 extends above the second cylindrical segment 155 and has a diameter substantially the same as the diameter of the second cylindrical segment 155. A second center channel 154 extends through the entire outer housing 150.

A second peripheral groove 161 is formed between second and third cylindrical segments 155, 157, and is arranged to receive a second lower seal 164 adapted to engage an inner surface 165 of the center channel 144. The second and third cylindrical segments 155, 157 are arranged to form a substantially small gap 167 from the inner surface 165, as both the second and third cylindrical segments 155, 157 are arranged to be fully received within the center channel 144. A cavity 166 is formed within the center channel and delimited at least in part from an upper surface of the third cylindrical surface. Air can travel in and out of the socket by the arrangement of the housing, such that a one-way valve is not necessary. Alternatively, a fluid regulator (not shown) may be placed and secured within the cavity 166.

The inner and outer mounting plates 120, 130 are secured to one another by fasteners 170 arranged to extend through alignment holes 171, 172 belonging to the inner and outer mounting plates 120, 130, respectively. The fasteners 170 may secure similarly to securing holes 126 of the inner mounting plate 120, as in the embodiment of FIG. 1, and extend through alignment holes 136 formed by the outer mounting plate 130. A clearance 168 is formed between the inner and outer mounting plates 120, 130, and generally filled by material of the outer retainer 114.

Figure 10:
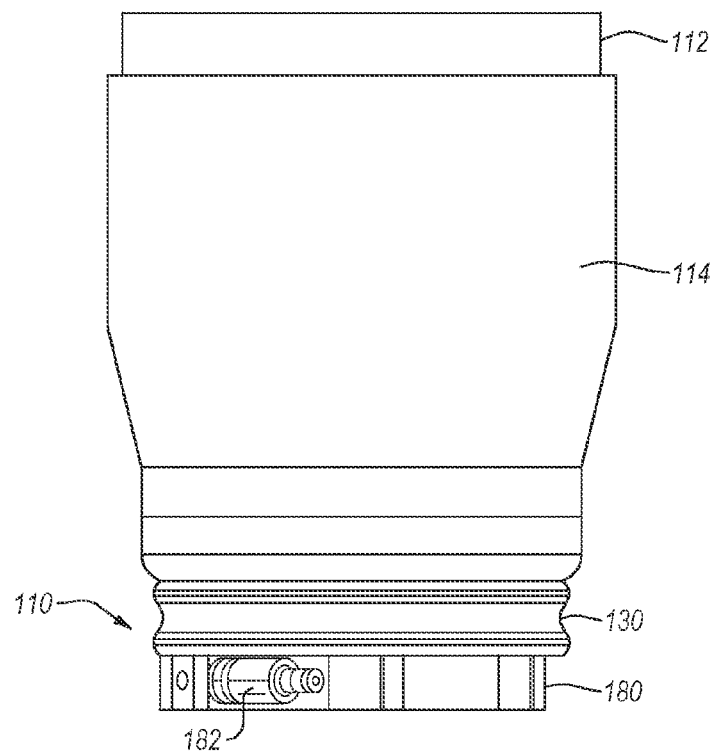
FIG. 10 is a side elevational view showing a seal plate secured to the mounting plate assembly of FIG. 8.
Figure 11:
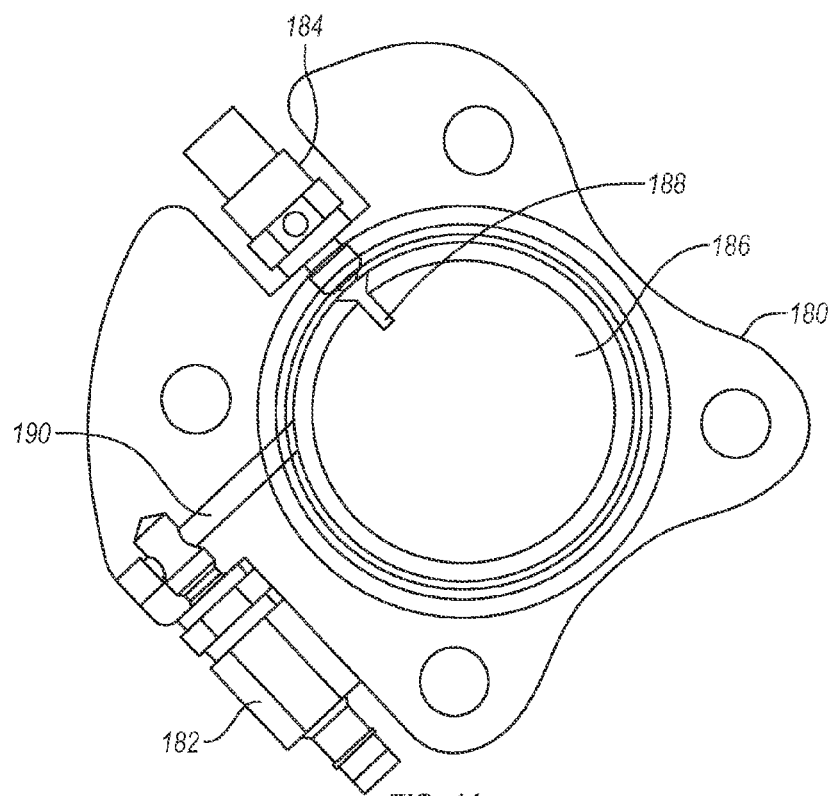
FIG. 11 is a top plan view of the seal plate of FIG. 10.

Referring to FIGS. 10 and 11, a push button seal plate 180 is secured to the outer mounting plate 130. The seal plate 180 is arranged for internal socket seal systems which create an internal seal between a prosthetic liner, such as the aforementioned, and the socket 110. The seal plate 180 may be a commercially available seal plate such VSP-002 sold by Evolution Industries of Orlando, Fla.

The seal plate 180 has a reservoir 186 arranged to extend the life of the socket by forming a reservoir for a vacuum. A push button release 184 is provided with the seal plate and operates within a channel 188 to let air into the socket to enable the user to get out of the socket. A valve 182, such as a one-way valve, connects to a pump for augmenting the vacuum created by the prosthetic assembly and allows air to escape from a distal end of the socket through the mounting plate system as a user places the residual limb into the socket. Various pumps, such as hand pumps, or simple expulsion systems may be used in combination with the valve 182 to provide an elevated vacuum. A seal may be provided between the seal plate and the outer mounting plate 130 to prevent air loss.

The mounting plate assembly may be provided with other seals and optionally peripheral grooves for receiving at least in part portions of the seals for better accommodating fabrication limitations of the socket, and volume fluctuations and other variables during ambulation.

While the foregoing embodiments have been described and shown, alternatives and modifications of these embodiments, such as those suggested by others, may be made to fall within the scope of the disclosure. While the prosthetic device has been described with a leg prosthesis, it will be understood that the principles described may be extended to other types of prosthetic devices.

The invention claimed is:

1. A mounting plate assembly for a prosthetic device, comprising:
    an inner housing having a first center channel defined along a central axis;
    a fluid regulator;
    an outer housing having a second center channel defined along the central axis and having an upper portion extending at least in part within the first inner channel, and a lower portion coupled to the fluid regulator wherein the second center channel opens into the fluid regulator;
    an inner mounting plate having a first center opening defined along the central axis, the first center opening arranged to receive at least a portion of the inner housing;
    an outer mounting plate having a second center opening defined along the central axis, the second center opening arranged to receive at least a portion of the outer housing;
    wherein the inner and outer mounting plates define a plurality of corresponding holes for receiving a plurality of fasteners for securing to the inner and outer mounting plates.

2. The mounting plate assembly of claim 1, characterized in that the inner housing defines a first engagement portion arranged to be received by and closely conform to at least a portion of the first center opening.

3. The mounting plate assembly of claim 2, characterized in that the inner mounting plate defines a square shape, with the first center opening formed centrally within the square shape.

4. The mounting plate assembly of claim 1, characterized in that the outer housing defines a second engagement portion arranged to be received by and closely conform to at least a portion of the second center opening.

5. The mounting plate assembly of claim 4, characterized in that the second center opening defines a recessed portion into which the second engagement portion fits, a bottom surface of the outer housing arranged flush relative to a bottom surface of the outer mounting plate.

6. The mounting plate assembly of claim 4, characterized in further comprising a first lower seal carried by the second engagement portion and arranged to secure against a portion of the outer mounting plate.

7. The mounting plate assembly of claim 1, characterized in that the outer housing defines a shoulder portion defining a base of the outer housing, a second engagement portion extends upwardly from the shoulder portion and a plurality of cylindrical portions extending from the second engagement portion, at least two of the cylindrical portions having a different diameter from one another with a lower cylindrical portion having a greater diameter than at least one upper cylindrical portion, the plurality of cylindrical portions arranged to extend within and be received by the first center channel.

8. The mounting plate assembly of claim 7, characterized in that the fluid regulator includes a one-way valve and a release mechanism sharing a reservoir formed by a seal plate.

9. The mounting plate assembly of claim 7, characterized in further comprising a second lower seal carried by the at least one upper cylindrical portion, and arranged to engage the first center channel.

10. The mounting plate assembly of claim 9, characterized in that the at least one upper cylindrical portion defines first and second segments spaced apart by a peripheral groove adapted to receive the second lower seal.

11. The mounting plate assembly of claim 1, characterized in that the inner and outer mounting plates are spaced apart by a clearance.

12. A prosthetic device, comprising:
a socket arranged for receiving a residual limb;
a mounting plate assembly received at and secured to a distal portion of the socket and including:
an inner housing having a first center channel defined along a central axis;
an outer housing having a second center channel defined along the central axis;
a fluid regulator coupled to the inner and outer housings, and defined along the central axis (B-B);
an inner mounting plate having a first center opening defined along the central axis, the first center channel arranged to receive at least a portion of the inner housing;
an outer mounting plate having a second center opening defined along the central axis, the second center channel arranged to receive at least a portion of the outer housing;
wherein the inner and outer mounting plates define a plurality of corresponding holes for receiving a plurality of fasteners for securing to the inner and outer mounting plates.

13. The prosthetic device of claim 12, further comprising:
a flexible insert having distal and proximal portions, and a cavity for receiving a residual limb;
a rigid outer retainer surrounding the distal portion of the insert;
wherein the inner housing extends into co-axial apertures formed by the distal portion of the insert and a distal portion of the outer retainer.

14. The prosthetic device of claim 13, wherein the inner mounting plate is received by a recess formed by the outer retainer.

15. A mounting plate assembly for a prosthetic device, comprising:
an inner housing having a first center channel defined along a central axis;
a fluid regulator including a one-way valve and a release mechanism sharing a reservoir formed by a seal plate;
an outer housing having a second center channel defined along the central axis and having an upper portion extending at least in part within the first inner channel, and a lower portion coupled to the fluid regulator wherein the second center channel opens into the fluid regulator;
wherein the outer housing defines a shoulder portion defining a base of the outer housing, a second engagement portion extends upwardly from the shoulder portion and a plurality of cylindrical portions extending from the second engagement portion, at least two of the cylindrical portions having a different diameter from one another with a lower cylindrical portion having a greater diameter than at least one upper cylindrical portion, the plurality of cylindrical portions arranged to extend within and be received by the first center channel.

* * * * *